US009211230B2

(12) United States Patent
Armm

(10) Patent No.: US 9,211,230 B2
(45) Date of Patent: Dec. 15, 2015

(54) LOWER BACK ACUPRESSURE DEVICE

(71) Applicant: Brendan Armm, Santa Monica, CA (US)

(72) Inventor: Brendan Armm, Santa Monica, CA (US)

( * ) Notice: Subject to any disclaimer, the term of this patent is extended or adjusted under 35 U.S.C. 154(b) by 190 days.

(21) Appl. No.: 13/871,799

(22) Filed: Apr. 26, 2013

(65) Prior Publication Data

US 2013/0317539 A1 Nov. 28, 2013

Related U.S. Application Data

(60) Provisional application No. 61/639,005, filed on Apr. 26, 2012.

(51) Int. Cl.
*A61F 5/08* (2006.01)
*A61H 39/04* (2006.01)

(52) U.S. Cl.
CPC .......... *A61H 39/04* (2013.01); *A61H 2201/165* (2013.01); *A61H 2201/168* (2013.01); *A61H 2201/1623* (2013.01); *A61H 2201/1695* (2013.01); *A61H 2205/081* (2013.01)

(58) Field of Classification Search
CPC ........... A61H 1/00; A61H 7/00; A61H 7/007; A61H 39/00; A61H 39/02; A61H 39/04; A61H 2201/0153; A61H 2201/0157; A61H 2201/1623; A61H 2203/00; A61H 2205/00; A61H 2205/081; A61H 2201/1695
USPC ........ 606/204, 189; 601/56, 107, 111, 97, 98, 601/104, 134, 136, 137; 604/289, 316; 602/19, 2, 60; D24/111, 112, 114
See application file for complete search history.

(56) References Cited

U.S. PATENT DOCUMENTS

| | | | | |
|---|---|---|---|---|
| 4,411,258 | A * | 10/1983 | Pujals, Jr. | 601/134 |
| 5,290,307 | A | 3/1994 | Choy | |
| 5,445,647 | A | 8/1995 | Choy | |
| 5,551,085 | A * | 9/1996 | Leighton | 2/44 |
| 5,836,653 | A * | 11/1998 | Albecker | 297/452.31 |
| 5,913,839 | A * | 6/1999 | Wincek | 601/134 |
| 5,938,684 | A | 8/1999 | Lynch et al. | |
| 6,528,697 | B1 * | 3/2003 | Knutson et al. | 602/54 |
| 6,711,750 | B1 | 3/2004 | Yoo | |
| 7,882,574 | B2 * | 2/2011 | Arsenault et al. | 2/227 |
| 2003/0227201 | A1 * | 12/2003 | Keilhauer | 297/230.1 |
| 2007/0060851 | A1 * | 3/2007 | Ferber et al. | 601/99 |
| 2009/0124941 | A1 * | 5/2009 | Lev | 601/134 |
| 2010/0179460 | A1 * | 7/2010 | Tsai | 601/134 |

* cited by examiner

*Primary Examiner* — Melanie Tyson
*Assistant Examiner* — Mikail Mannan
(74) *Attorney, Agent, or Firm* — Dicke, Billig & Czaja, PLLC

(57) ABSTRACT

An acupressure device for promoting healing includes a plate having a frame, a vertical center plane and independently moving left and right wings attached to the frame. Three horizontal pairs of acupressure protrusions are affixed on the left and right wings, each protrusion affixed equal-distant from the vertical center plane. A fourth horizontal pair of acupressure protrusion is affixed to a bottom portion of the frame, both protrusions affixed equal-distant from the vertical center plane. Finally, a fifth horizontal pair of acupressure protrusions is affixed on the left and right wings and positioned vertically between a lowest and a second lowest pair of the first four pairs of protrusions and is centered about the vertical center plane at a horizontal distance greater than a horizontal distance of the first four pairs of protrusions.

16 Claims, 6 Drawing Sheets

LOWER BACK ACUPRESSURE DEVICE

CROSS-SECTION TO RELATED APPLICATION

This application claims the benefit under 35 U.S.C. §119 (e) of U.S. Provisional Patent Application No. 61/639,005, filed Apr. 26, 2012, which is incorporated herein by reference in its entirety and for all purposes.

TECHNICAL FIELD

The present invention relates generally to the field of medicine, including pain relief and healing. In particular, the present invention relates to oriental medicine, specifically lower back acupressure.

BACKGROUND

Acupressure is an ancient healing art that uses localized and direct pressure on acupuncture points and meridians to release muscle pain and tension, and to increase circulation. Acupressure has been used to alleviate pain and promote healing throughout the body in Chinese medicine for centuries. Traditional Chinese medicine focuses on natural healing and the shifting of energy throughout the body to relieve pain and increase overall wellness. Only recently has western culture begun looking into acupressure as a healing tool.

Acupressure points, also called potent points, are places on the surface of a body that are especially sensitive to bioelectrical impulses in the body and conduct those impulses readily. When stimulated, these acupressure points may also stimulate coordinating organs and muscles. Stimulating acupressure points triggers the release of endorphins which are the neurochemicals that relieve pain. As a result, pain is blocked and the flow of blood and oxygen to the affected area is increased. This causes the muscles to relax and promote healing.

Besides relieving pain, acupressure may help rebalance the body by dissolving tensions and stresses that keep it from functioning smoothly and that inhibit the immune system. Acupressure also enables the body to adapt to environmental changes and resist illness.

As an acupressure point is stimulated, the muscle tension yields to the pressure, enabling the fibers of the muscle to elongate and relax, blood to flow freely, and toxins to be released and eliminated. Increased circulation also brings more oxygen and other nutrients to affected areas, thereby increasing the body's resistance to illness.

In order for acupressure therapy to be effective, the pressure points must be identified and contacted with precision and sufficient pressure. In addition, it may be necessary for the pressure to be applied over a continued period of time. Manual application of pressure is subject to short comings, especially when it is attempted by a user, because of difficulties in locating the appropriate pressure points, as well as difficulties associated with the continuous maintenance of pressure on the desired point over an extended period of time. Further, in many instances, it is appropriate to apply acupressure to numerous acupressure points at the same time.

A common area for acupressure therapy is the lower back of a user. The lower back contains numerous acupressure points. U.S. Pat. No. 5,445,647, entitled "Spinal Acupressure Device," discloses a device for a user to attempt to provide pressure to multiple pressure points in the back of a user. The '647 patent discloses a flat pad or plate having two rows of four projections projecting from the pad or plate, all on two flat strips. The design in the '647 patent does not take into consideration the natural curve of the lumbar spine or the lumbar spine's connection with the sacrum (tailbone). Further, the '647 patent focuses on lumbar vertebras 1-4 (L1-L4) and does not address two of the most common locations for lower back pain, which include lumbar vertebra 5/sacral 1 (L5/S1) and the sacroiliac joint.

U.S. Pat. No. 4,411,258, entitled "Method and Device for Relieving Pain," discloses a flat pad or plate having projections projecting from the pad or plate. The device disclosed in the '258 patent has many short comings. First, the protrusions are not uniquely placed to target acupressure points in the back of a user. Second, the device does not allow for need curvature of the lower back and sacrum to be effective in treating lower back pain. Third, the protrusions have a height of only about 0.125 inches and a base diameter of only about 0.125 inches, which are incapable of providing the depth of pressure needed at acupressure points to provide meaningful muscle pain relief or increased circulation.

SUMMARY

A lower back acupressure device for alleviating pain has been developed. The acupressure device alleviates lower back and sacroiliac pain by stimulating acupressure points within the user and triggering the release of endorphins which are neurochemicals that relieve pain. Thus, pain is blocked and the flow of blood and oxygen to an affected area is increased. This may cause the affected related muscle(s) to relax and promote healing. Further, the acupressure device may help to rebalance the body of a user by dissolving tensions and stress that keeps the body from functioning optimally and that inhabits the immune system. The acupressure device may also enable the body to adapt to environmental changes and resist illness. In addition, when properly positioned on a lower back of a user, the acupressure device decreases muscle tension associated with a stimulated acupressure point, enabling the fibers of the muscle to elongate and relax, blood to flow more freely, and toxins to be released and eliminated. Increased circulation brings more oxygen and other nutrients to the affected area for the purpose of healing and pain relief.

In one embodiment, a lower back acupressure device for alleviating lower back and sacral-iliac pain includes a plate having a frame, a vertical center plane, and independently moving left and right wings attached to the frame. The acupressure device includes three horizontal pairs of acupressure protrusions, each pair of protrusions consisting of a left protrusion affixed to the left wing horizontally equal distant from the vertical center plane and a corresponding right protrusion affixed to the right wing horizontally equal distant from the vertical center plane. A fourth horizontal pair of protrusions consists of a left protrusion affixed to a bottom portion of the frame left of the vertical center and a right protrusion affixed to the bottom portion of the frame right of the vertical center. These four horizontal pairs of protrusions are positioned on the device such that all of the left protrusions are aligned in a vertical plane and all of the right protrusions align in another vertical plane. Further, the lower back acupressure device includes a fifth horizontal pair of acupressure protrusions consisting of a left protrusion affixed to the left wing and a right protrusion affixed to the right wing such that this fifth horizontal pair of protrusions is positioned vertically between the lowest and the second lowest pair of previously described protrusions and centered about the vertical center plane at a horizontal distance greater than the horizontal distance of the four pairs of previously described acupressure protrusions.

The present invention further provides the lower back acupressure device having a belt detachably affixed to the plate for securing the plate to a person at a proper location and a proper pressure. Ideally, the belt secures the device to a person such that the vertical center of the plate is aligned with the spine of the person. Further, if properly positioned, the device will be secured to a person by the belt such that the two lowest pairs of horizontal acupressure protrusions are positioned adjacent to a sacrum and an iliac bone of the user and the remaining three pairs of horizontal protrusions are positioned adjacent a junction of lumbar vertebra 5/sacral 1 (L5/S1), lumbar vertebra 4/lumbar vertebra 5 (L4/L5), and lumbar vertebra 2/lumbar vertebra 3 (L2/L3).

The present invention further provides the left and right wings are each capable of independent movement or flexing with respect to the other wing, so as to maintain or apply additional pressure, one side at a time, while the user is walking or moving. This individual movement or flexing of the saloon door style device also improves contouring capability for various body types, and is more comfortable to wear than prior rigid, solid designs.

In another embodiment of the present invention, a lower back acupressure device for alleviating lower back and sacral iliac pain includes a plate having a contoured top surface and a vertical center plane. The device further includes four pairs of acupressure protrusions, each pair centered about the vertical center plane of the top surface of the plate. Further, the device includes a fifth pair of acupressure protrusions located vertically between the lowest and the second lowest pair of acupressure protrusions and centered about the vertical center plane at a horizontal distance greater than the horizontal distance of the four other pairs of acupressure protrusions.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "left," "right," "leading," "trailing," etc., is used with reference to the orientation of the Figure(s) being described. Because components of embodiments may be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

FIGS. 1-4 are a front view, a back view, a side view, and a perspective view of acupressure device 100 in accordance with one embodiment of the present invention, respectively. Acupressure device 100 may be a device for healing and utilized to provide pain relief and/or promote healing and wellness when properly attached to a user. Acupressure device 100 may be attached at various locations to a user, including, in one embodiment, the lower back of a user, to provide pain relief and promote healing and wellness of the user. In one embodiment, acupressure device 100 is a substantially horizontal oriented plate; as opposed to vertical oriented plates such as plate 200, to cover a greater width of the lumbar region of a user.

Figure 2:
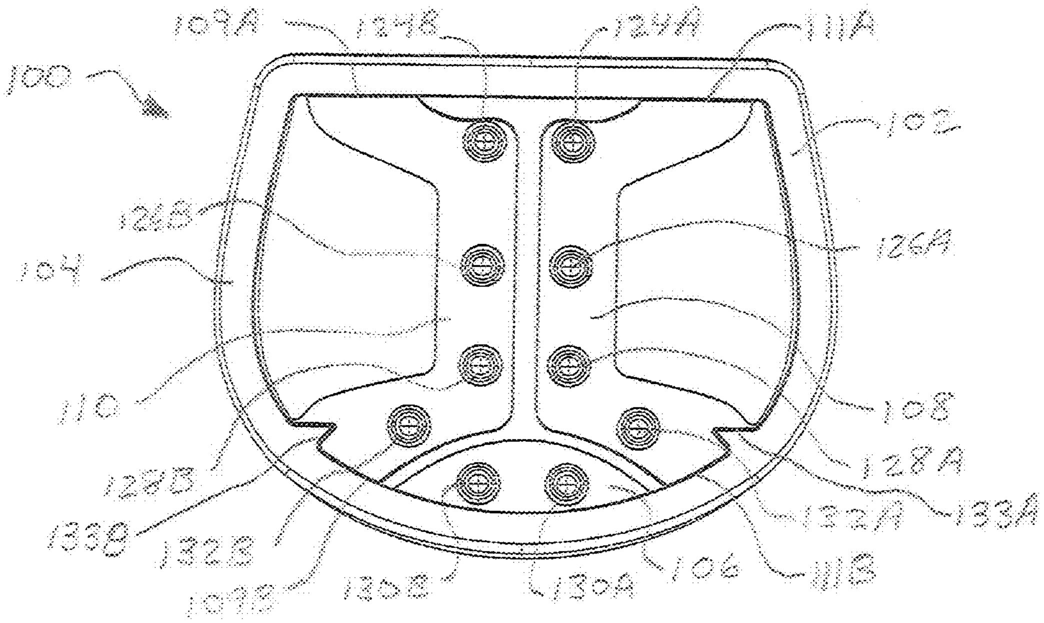
FIG. 2 is a back view of an acupressure device in accordance with one embodiment of the present invention.
Figure 3:
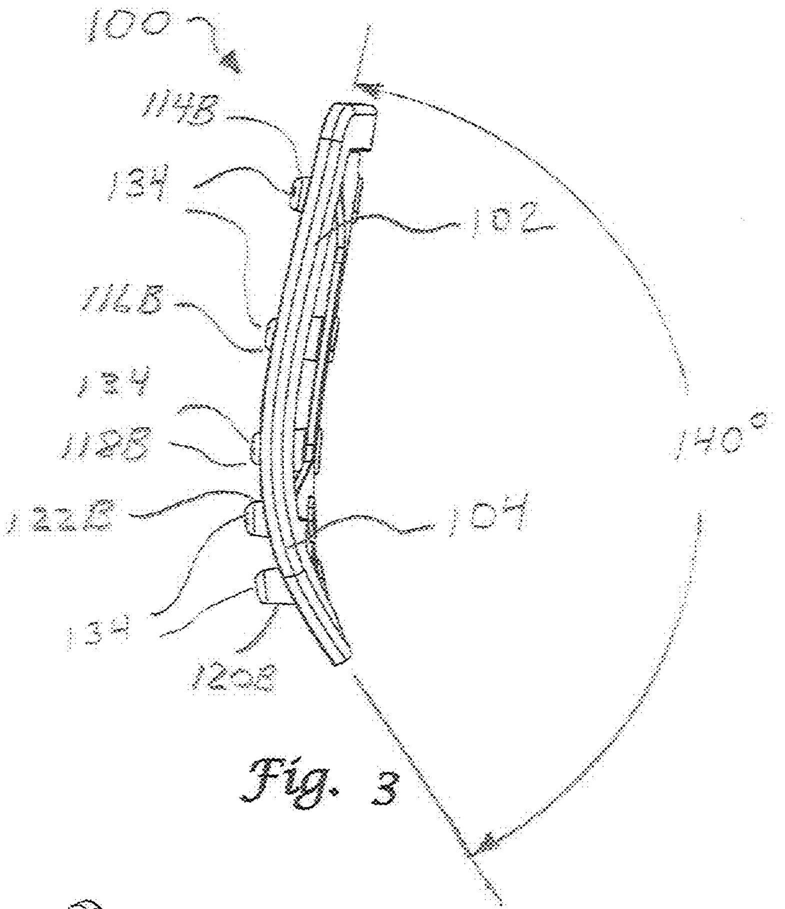
FIG. 3 is a side view of an acupressure device in accordance with one embodiment of the present invention.
Figure 4:
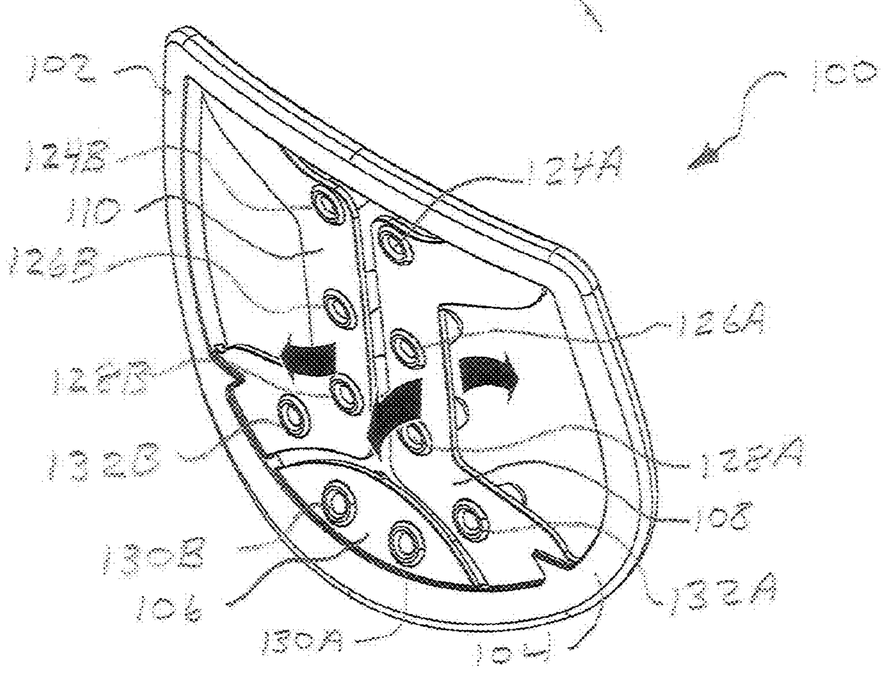
FIG. 4 is a perspective view of an acupressure device in accordance with one embodiment of the present invention.

As shown in FIGS. 1-4, acupressure device 100 includes saloon door style plate 102 having outer frame 104 and bottom extension 106 of outer frame 104. Acupressure device 100 further includes left wing 108 having connection points 109A and B and right wing 110 having connection points 111A and B. Left and right wings 108 and 110 are permanently attached to outer frame 104 of plate 102 at connection points 109A and B and 111A and B, respectively. Vertical center plane 112 is shown to highlight that the left and wing halves of acupressure device 100 are identical to each other. It is understood that vertical center plane 112 is not a physical element of acupressure device 100; vertical center plane 112 merely highlights the symmetry of acupressure device 100. Left wing 108 is capable of independent movement or independent flexing, as represented in FIG. 4 at least by the bold arrows. As such, left wing 108 is capable of independent movement or flexing with respect to right wing 110, as well as with respect to outer frame 104 and bottom extension 106 of outer frame 104. Likewise, right wing 110 is capable of independent movement or independent flexing, as represented in FIG. 4 at least by the bold arrows. As such, right wing 110 is capable of independent movement or flexing with respect to left wing 108, as well as with respect to outer frame 104 and bottom extension 106 of outer frame 104.

Acupressure device 100 also includes acupressure protrusion pairs 114A, 114B, 116A, 116B, 118A, 118B, 120A, 120B and 122A, 122B. As shown in FIGS. 1-4, acupressure protrusion pairs 114, 116 and 118 are affixed to left wing 108 and right wing 110 such that one acupressure protrusion of each pair is located on left wing 108 and one acupressure protrusion from each acupressure protrusion pair is located on right wing 110. Acupressure protrusion pair 120 is affixed to bottom extension 106 of outer frame 104. Acupressure protrusion pair 122 is affixed to left and right wings 108, 110, such that one acupressure protrusion is affixed to left wing 108 and one acupressure protrusion is affixed to right wing 110. Each pair of acupressure protrusions 114-122 are horizontal acupressure protrusion pairs such that the two acupressure protrusions A, B of each acupressure protrusion pair are located horizontal to each other. When properly affixed to a user, such that the vertical center of plate 112 is aligned with a spine of the user, horizontal acupressure protrusion pairs 120A, 120B and 122A, 122B are positioned adjacent to a sacrum and an iliac bone of the user. The remaining three pairs of horizontal protrusion pairs 118A, 118B, 116A, 116B and 114A, 114B are positioned adjacent a junction of lumbar vertebra 5/sacral 1 (L5/S1), lumbar vertebra 4/lumbar vertebra 5 (L4/L5) and lumbar vertebra 2/lumbar vertebra 3 (L2/L3), respectively.

Acupressure protrusion pairs 114-122 may be affixed to acupressure saloon door style plate 102 in any known means, either permanently or temporarily. In one embodiment, the entire acupressure device 100 is formed in a single mold or fabrication of medium to hard plastic, such as material similar to a dashboard of an automobile. In another embodiment, outer frame 104, bottom extension of outer frame 106, left wing 108 and right wing 110 are formed of a single mold, and acupressure protrusion pairs 114-122 are later attached via known means.

Each acupressure protrusion of acupressure protrusion pairs 114-122 have a height greater than 0.50 inches, and preferably in the range of approximately 0.625 inches to 0.750 inches, and more preferably have a height of approximately 0.6875 inches. In addition, as shown in FIG. 3, each acupressure protrusion is tapered from a base of the protrusion to a tip of the protrusion, such that a diameter of the tip is smaller than a diameter of the base, and each acupressure protrusion has debossed tip 134. The height and the design of each acupressure protrusion 114-122 ensures that when properly attached to a user, acupressure points in the lower back of the user are properly stimulated by acupressure protrusions 114-122. Acupressure protrusions having a height less than 0.50 inches may not properly apply pressure to and stimulate acupressure points in the user, thereby minimizing the pain relief, healing and wellness effects of acupressure device 100.

It is understood that the specific terms used to identify elements of acupressure device 100 should not be construed in a limiting way. For example, plate 102 represents any type of support vessel; left and right wings 108 and 110 represent any type of moving instrument; acupressure protrusions 114-122 represent any type of applicable therapeutic agents, including, but not limited to, medicinal aid(s) or a patch or fabric material having or capable of containing a medicinal aid; and belt 140 (shown and described with reference to FIGS. 5 and 6) represents any type of support or securing mechanism including, but not limited to, a belt, a patch, or fabric material.

FIG. 2 illustrates the back of acupressure device 100. As shown in FIG. 2, location identifiers 124A, 124B, 126A, 126B, 128A, 128B, 130A, 130B and 132A, 132B are shown at identical locations to acupressure protrusion pairs 114-122, respectively. Location identifiers 124-132 aid the user in correctly positioning acupressure device 100 on his/her lower back. In addition, belt guide markers 133A and B aid the user in assuring proper location of a belt (Belt 140 further described with reference to FIGS. 5 and 6) to be used to secure acupressure device 100 to the lower back of a user. Belt guide markers 133A and B provide a small or minor edge for the bottom of the belt to rest on, thereby ensuring the proper vertical location of the belt during attachment and use by the user. In one embodiment, the belt opening between belt opening points 136A and B, as well as the belt opening between belt opening points 136C and D, is greater than 4.0 inches to accommodate a 4.0 inch belt, and preferably in the range of approximately 4.01 inches to 4.50 inches, and more preferable 4.19 inches. However, the belt opening, as well as the belt, may be different dimensions, based on the desired application, without deviating from the present invention.

As shown in FIG. 3, outer frame 104 of acupressure device 100 is contoured such that the contoured slop of acupressure device 100 more accurately replicates an actual normal lumbar curvature of an adult user, thereby providing a correct anatomical fit to the lower back of the user. The lower part of plate 100 flares out away from the surface contain acupressure protrusions 114-122 such that the angle of curvature between the top portion of acupressure device 100 and the bottom portion of acupressure device 100 is between 120° and 160°, ideally approximately 140°.

As shown in FIG. 4 at least by the bold arrows, left wing 108 and right wing 110 are each capable of independent movement or flexing, similar to a saloon door design. Connection points 109A and B and 111A and B of left wing 108 and right wing 110, respectively, shown in FIG. 1, act as hinges permitting independent movement or flexing of each wing, independent of the other wing and independent of outer frame 104. Thus, when properly affixed to the lower back of a user, left and right wings 108, 110 may move or flex independent of each other and of outer frame 104 due to movement of the user, such as walking, running, twisting, bending, reaching, etc.

Figure 1:
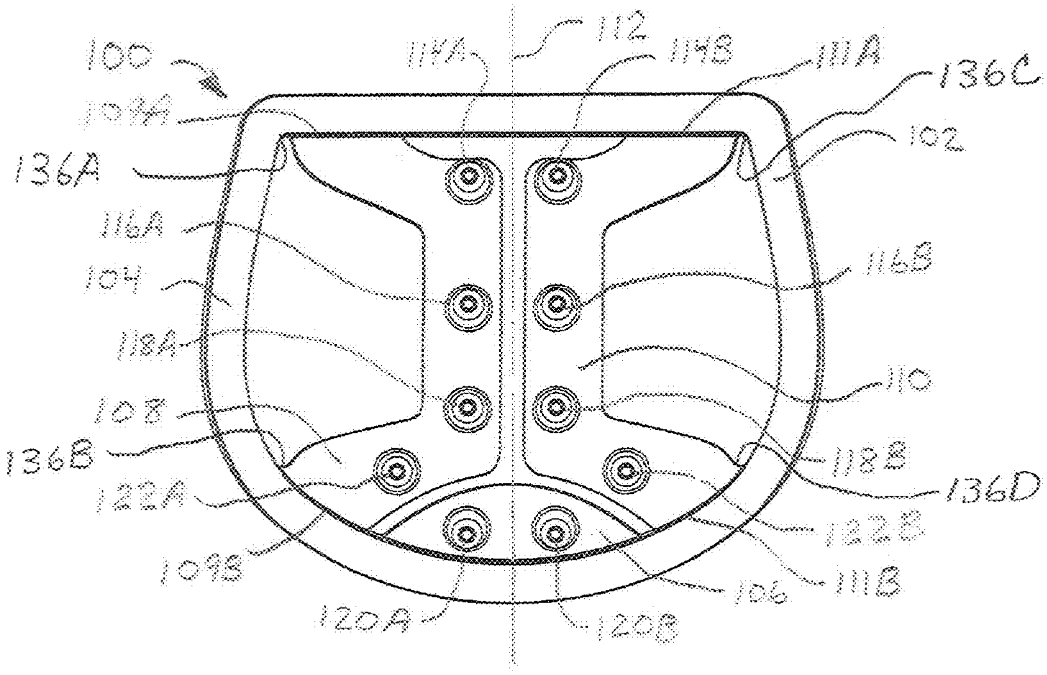
FIG. 1 is a front view of an acupressure device in accordance with one embodiment of the present invention.

As shown in FIGS. 1 and 2, acupressure protrusion pair 122 is located horizontally wider than acupressure protrusion pairs 114-120, which are located horizontally equal to one another. Acupressure protrusion pair 122, when acupressure device 100 is properly attached to the lower back of a user, corresponds to identified acupressure points of the sacroiliac joint which, when properly stimulated, provides additional pain relief and promotion of healing and wellness as compared to providing adequate pressure to pressure points associated with acupressure protrusion pairs 114-120 alone.

Figure 5:
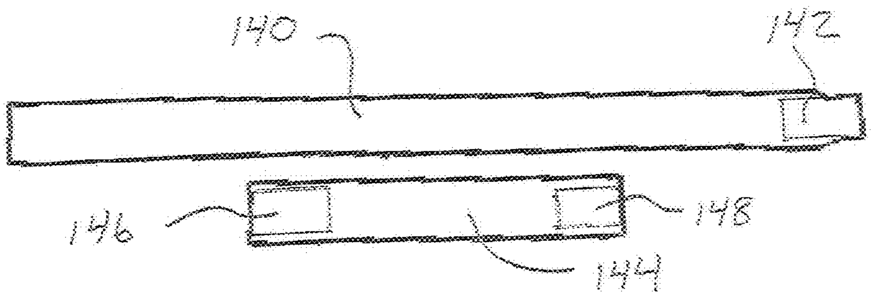
FIG. 5 is a view of the inside of an attaching and support devices in accordance with one embodiment of the present invention.
Figure 6:
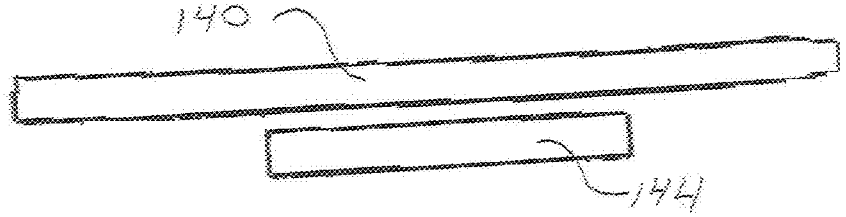
FIG. 6 is a view of the outside of an attaching and support devices in accordance with one embodiment of the present invention.

FIGS. 5 and 6 are top views of both the inside of belt 140 and turbo adaptor support 144. Belt 140 includes Velcro strip 142, while turbo adaptor 144 includes Velcro adaptors 146 and 148. Belt 140 is used to secure acupressure device 100 to the back of a user. Belt 140 may be permanently or temporarily affixed to acupressure device 100. In one embodiment, belt 140 is inter-looped to acupressure device 100 and wrapped around the user. Belt guide markers 133A and B (showing in FIG. 2) provide for directional guidance for the lower edge of belt 140. Further, the lower edge of the top portion of outer frame 104 provides for directional guidance for the upper edge of belt 140. In one embodiment, belt 140 may be connected to device 100 by threading belt 140 in front of the inner edge of the side portion of outer frame 104 near wing 108, continuing behind left and right wings 108, 110, and in front of the opposite side inner edge of the side portion of outer frame 104 near wing 110. It is understood that belt 140 may be connected to device 100 in the opposite direction, such as moving in the direction from right wing 110 to left wing 108, without deviating from the present invention.

Velcro strip 142 secures belt 140 to itself. Belt 140 should be sufficiently long enough to fit around the waist of the user. In one embodiment, belt 140 is approximately 4 inches wide and 56 inches long. In one embodiment, belt 140 is made of Neoprene material on one side and Tempo material on the other side. Velcro strip 142 is approximately 5 inches long and 3 inches wide and formed from Velcro. Belt 140 and acupressure device 100 are to be worn firmly around the waist and lower back and sacrum of a user, with acupressure device 100 held in place at the middle of the lower back and sacrum regions. Turbo adaptor 144 may be removably affixed to belt 140 in order to provide additional and isolated tightening pressure for the plate against the lower back/sacrum of a user without providing extra tightening pressure about the front and sides of the user. Turbo adaptor 144 is to be worn on top of belt 140 and acupressure device 100 and may be pulled from back to front on both sides of the body and attached to belt 140 via 5 inch long by 3 inch wide Velcro strips 146 and 148. In one embodiment, turbo adaptor 144 measures approximately 24 inches in length and 4 inches in width, and is preferably made from an elastic material. Belt 140 and turbo adaptor 144 may include Velcro to provide adequate attachment, as disclosed, or may include any other hook and loop system to provide adequate attachment.

When properly positioned on the lower back of a user via belt 140 with turbo adaptor 144 applying proper pressure, acupressure device 100 provides for adequate pressure to be applied to pressure points in the lower back/sacrum of the user. Acupressure points located near the spine of a user or located near the sacrum and iliac bone of the user are known to respond to applied pressure. Properly applied pressure to acupressure points in the back of a user, including acupressure points within a juncture of lumbar vertebra 5/sacral 1 (L5/S1), lumbar vertebra 4/lumbar vertebra 5 (L4/L5), lumbar vertebra 2/lumbar vertebra 3 (L2/L3) and adjacent to the sacrum and the iliac bone of the user facilitate increased circulation, including greater blood and oxygen profusion. Due to this increased blood and oxygen profusion, neurologically, the brain is stimulated, endorphins are released, pain is relieved and healing and wellness may be achieved. Further, proper location of acupressure protrusion pairs 114-122 may eliminate stagnation or unblock obstructions within the lower back of a user, thereby allowing greater circulation of blood and oxygen, thereby also providing pain relief, healing and wellness.

Further, when properly attached to the lower back of a user via belt 140, acupressure device 100 alleviates lower back and sacroiliac pain by stimulating acupressure points within the user and triggering the release of endorphins which are neurochemicals that relieve pain. Thus, pain is blocked and the flow of blood and oxygen to an affected area is increased. This may cause the affected related muscle(s) to relax and promote healing. Further, acupressure device 100 may help to rebalance the body of a user by dissolving tensions and stress that keeps the body from functioning optimally and that inhabits the immune system. Acupressure device 100 may also enable the body to adapt to environmental changes and resist illness. In addition, when properly positioned on a lower back of a user, acupressure device 100 decreases muscle tension associated with a stimulated acupressure point, enabling the fibers of the muscle to elongate and relax, blood to flow freely, and toxins to be released and eliminated. Increased circulation brings more oxygen and other nutrients to the affected area.

For long lasting relief, acupressure device 100 should be properly positioned on the lower back/sacrum of a user for one hour daily and not to be used while driving, when pregnant, while exercising, or when certain activities or medical conditions which might make using this belt dangerous to one's health. This process should be repeated for 30 consecutive days to promote long lasting effects and benefits. In one embodiment acupressure device 100 and belt 140 are detachable, which provides for ease of washing of belt 140 separate from acupressure device 100.

Figure 7A:
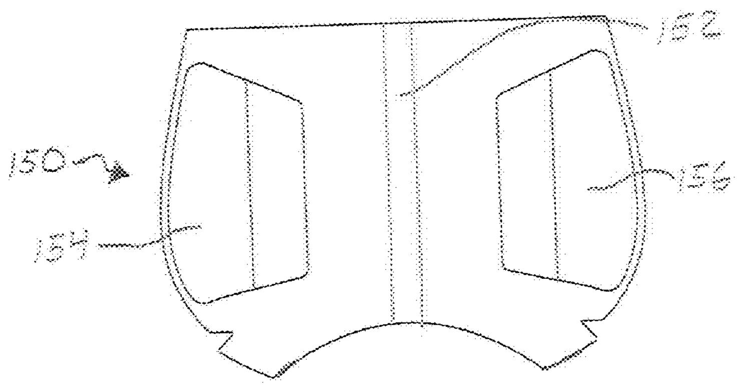
FIG. 7A is a top view of a butterfly hot/cold pack in accordance with another embodiment of the present invention.
Figure 7B:
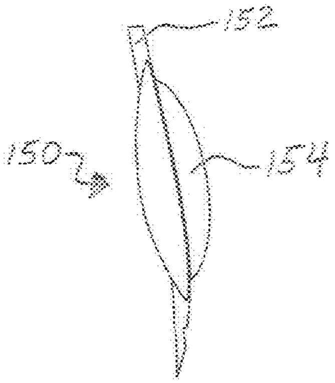
FIG. 7B is a side view of a butterfly hot/cold pack in accordance with another embodiment of the present invention.
Figure 8:
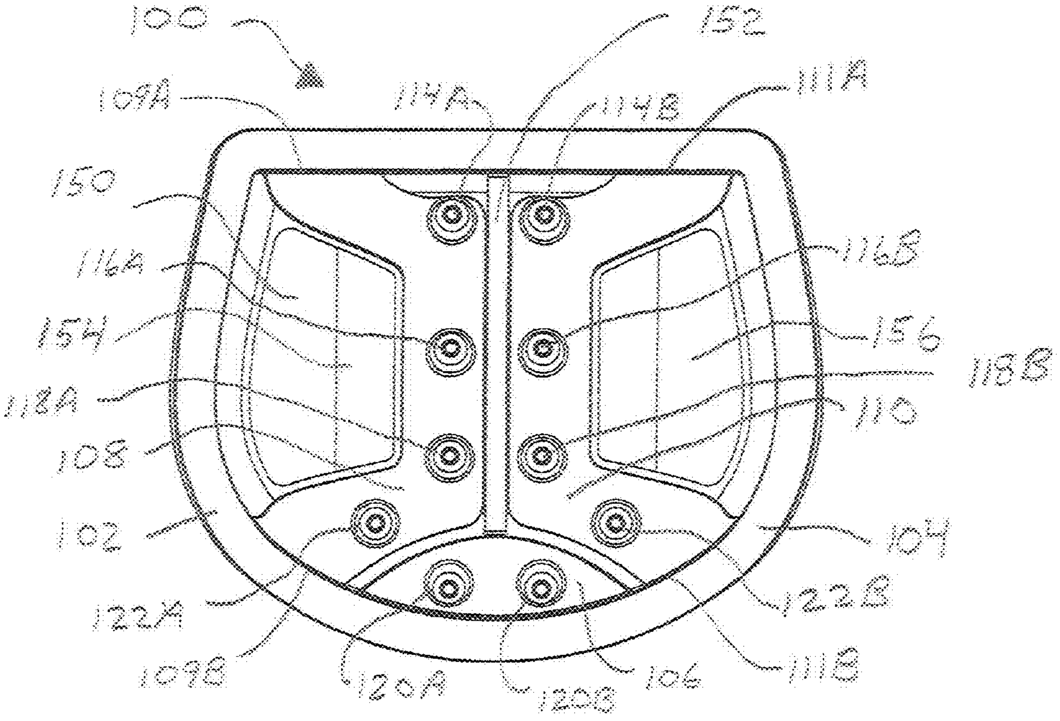
FIG. 8 is a front view of an acupressure device incorporating a hot/cold pack in accordance with another embodiment of the present invention.
Figure 9:
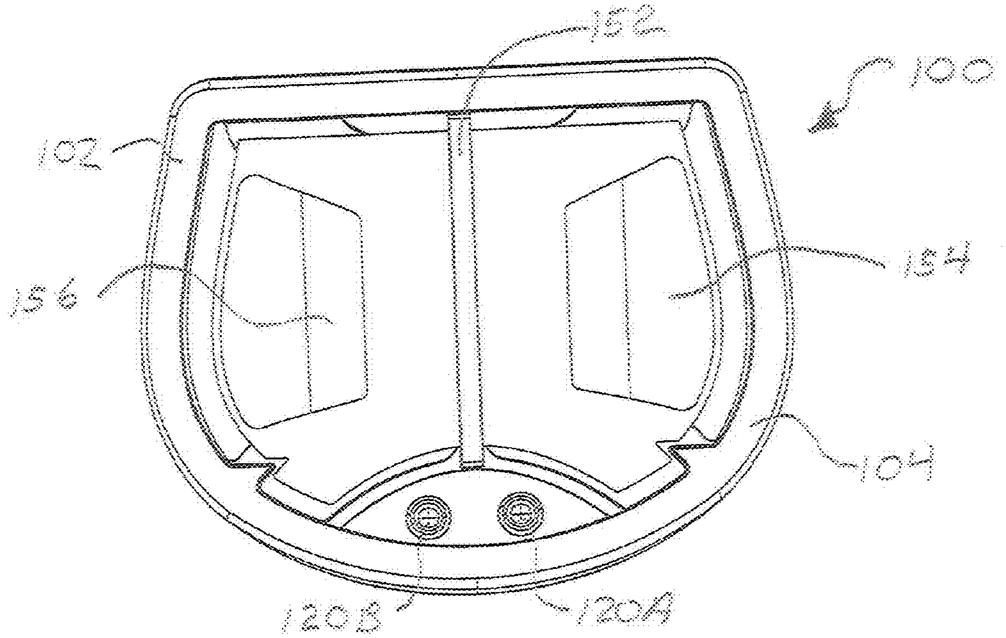
FIG. 9 is a back view of an acupressure device incorporating a hot/cold pack in accordance with another embodiment of the present invention.
Figure 10:
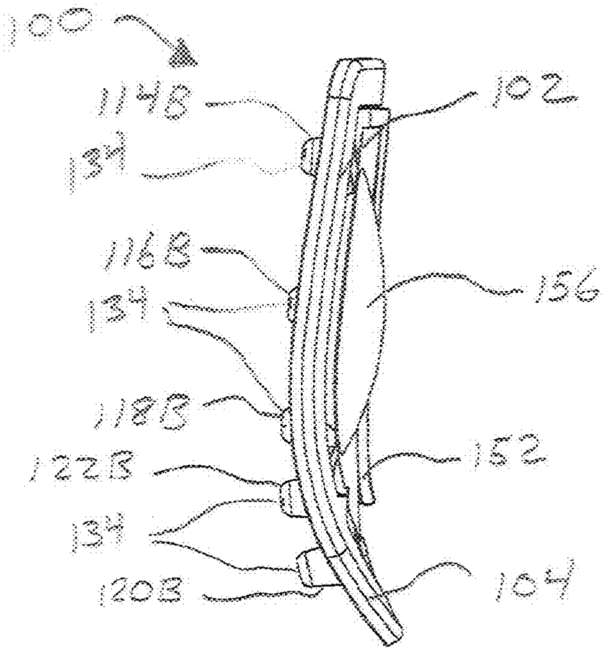
FIG. 10 is a side view of an acupressure device incorporating a hot/cold pack in accordance with another embodiment of the present invention.
Figure 11:
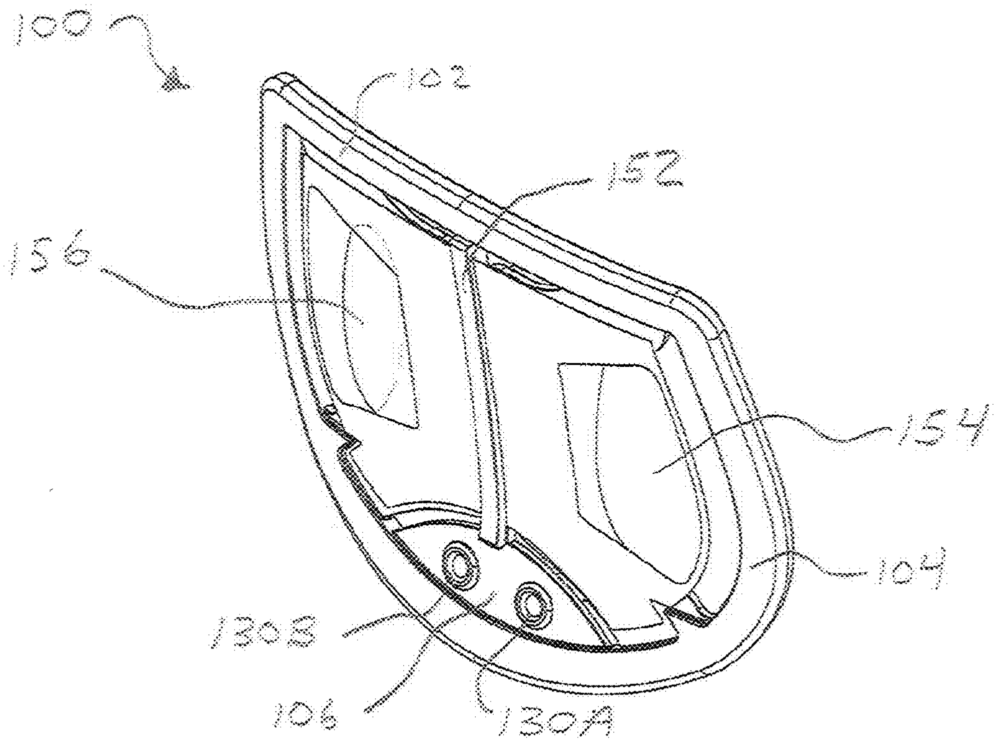
FIG. 11 is a perspective view of an acupressure device incorporating a hot/cold pack in accordance with another embodiment of the present invention.

FIGS. 7A and 7B illustrate a butterfly style dual hot/cold pack 150. Dual hot/cold pack 150 includes center clip 152 (which may be removable from or affixed to hot/cold pack 150), left hot/cold pack 154 and right hot/cold pack 156. Center clip 152 may be removable from or affixed to hot/cold pack 150. Center clip 152 may be releasably attached to dual hot/cold pack 150 by pinching center clip 152 such that a portion of dual hot/cold pack 150 in positioned within center clip 152. Further, center clip 152 may be removed from hot/cold pack 150 by releasing the pinch of center clip on dual hot/cold pack 150.

As shown in FIGS. 8-11, dual hot/cold pack 150 has been designed so that it may be secured to acupressure device 100 such that center clip 152 may be centrally positioned at vertical center plane 112 of acupressure device 100 between left wing 108 and right wing 110 and fits between left wing 108 and right wing 110 of acupressure device 100. Therefore, left and right hot/cold packs 154 and 156 may be positioned and secured within the spaces of saloon door style plate 102 of acupressure device 100. Belt 140 ensures that dual hot/cold pack 150 remains in proper position, as it weaves through sandwiching dual hot/cold pack 150 between itself and acupressure device 100, during uses such that left hot/cold pack 154 and right hot/cold packs 156 are properly positioned within the spaces of left wing 108 and right wing 110 of acupressure device 100, respectively. As left wing 108 and right wing 110 of acupressure device 110 are each capable of independent movement or flexing, left and right hot/cold packs 154 and 156 are also each capable of independent movement. Thus, similar to wings 108 and 110, hot/cold packs 154 and 156 are capable of maintaining contact with the back of the user, regardless of motion or movement. Dual hot/cold pack 150 may be heated or cooled by known means, such as including the use of a microwave, a refrigerator, a freezer, or hot or cold water. While Dual hot/cold pack 150 is shown as a single element having two distinct hot/cold packs, it is understood that two separate and distinct hot/cold packs may be used without deviating from the present invention.

In addition to the previously described acupressure points in the lower back of a user, additional acupressure points have been identified which are horizontally farther away from the spine of a user than acupressure points associated with acupressure protrusion pairs 114-120, and vertically above and possibly slightly lateral to acupressure points associated with acupressure protrusion pair 122. These additional acupressure points are sensitive to, and react to, hot and cold stimulation. Temperature stimulation to these identified pressure points, especially heat stimulation, may promote additional blood and oxygen profusion and may promote vasodilation wherein vessels affected by the change in temperature expand, thereby promoting greater circulation of both blood and oxygen, as well as promoting pain relief and healing. In addition, temperature stimulation may eliminate stagnation and unblock obstruction within muscles, blood and oxygen flow, and promote pain relief and healing. As such, dual hot/cold pack 150 is designed to target these additional acupressure points.

Figure 12:
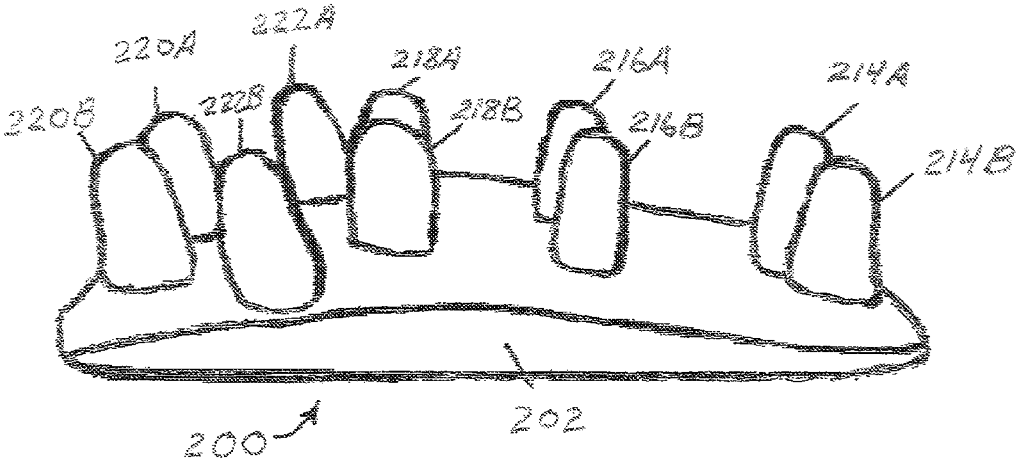
FIG. 12 is a side perspective view of an acupressure device in accordance with yet another embodiment of the present invention.

Referring now to FIG. 12, there is shown acupressure device 200 having curved plate 202 with affixed acupressure points 214-222 designed to treat lumbar 2/3 (L2/L3), lumbar 4/5 (L4/L5), and lumbar 5/sacral 1 (L5/S1) vertebral pain, as well as sacral-iliac pain. Affixed to curved plate 202 are ten uniform acupressure protrusions; points 220A and B and 222A and B are at the bottom to contour to the sacrum and it's connection to the iliac bone. Points 218A and B line up with the junction of lumbar vertebra 5 and Sacral 1 (L5/S1), whereas points 216A and B line up with lumbar vertebrae 4 and 5 junction (L4/L5). Finally, points 214A and B align with lumbar vertebrae 2 and 3 junction (L2/L3) in a region of the body known in Chinese medicine to be a command point for the lower back. Plate curve 202 shows the curve of the plate, and it's unique design to contour to the lower back. Plate 200 shown in FIG. 12 is adhered to belt 240 as shown in FIG. 13, perpendicular to the belt, which wraps around the lower waist of the user.

Figure 13:
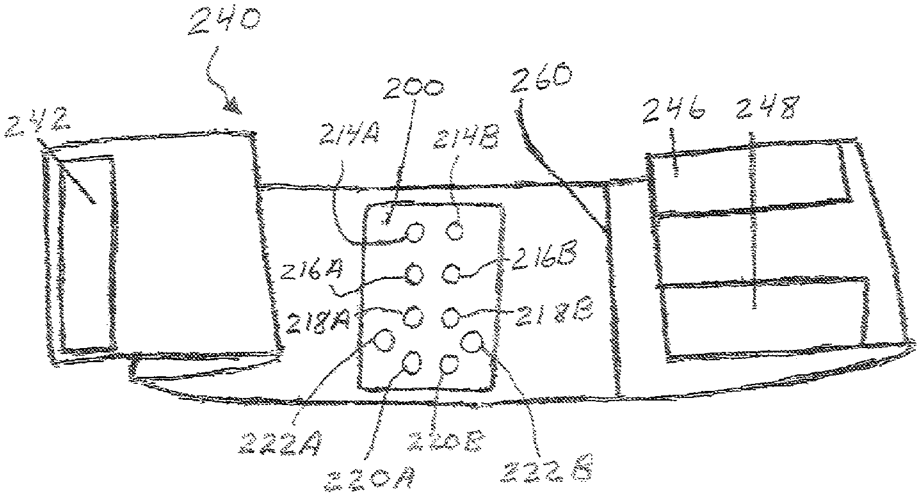
FIG. 13 is a top view of an acupressure device and support device in accordance with yet another embodiment of the present invention.

In more detail, belt 240 in FIG. 13 keeps plate 200 in place to the lower back and sacral region of the user. In regards to proper placement of belt 240 and plate 200 acupressure points 214-220 are aligned in two parallel lines next to each other. The lower back spine is to be positioned in between these parallel lines. To align the proper height of the belt 240, acupressure points 220A and B and 222A and B are to rest in the sacroiliac joint located medial to the outer hips where a natural depression lies in the skin. Once belt 240 is properly placed, Velcro strip 242 can be adjusted to a snug fit with Velcro 246 and 248. To confirm proper placement of belt 240 the wearer should feel all 10 acupressure points in the lower back and sacral iliac region of the body.

In further detail, still referring to the invention of FIGS. 12-13 to achieve results, the size of plate 200 is sufficiently long enough to cover the lower back and sacral iliac region, such as about 5.0 inches long and 3.5 inches wide, and the 0.375 inches at the height of the curve 202. The acupressure points 214-222 are sufficiently tall to apply the needed pressure for treating skin, muscle, tendon, nerve, cartilage and bone pain, such as about 0.6-1.0 inches in height and such as about 0.25-0.75 inches in diameter at the base. The tips of acupressure points 214-222 should be blunt and rounded like a finger, and not sharp which could otherwise pierce the skin.

Belt 240 has strips 260 to prevent wrap over of the belt 240 onto itself, and to allow belt 240 to curve slightly up fitting to the shape of the waist. Velcro strip (male end) 242 lines one end of the belt 240, and attaches around the waist to Velcro strip (female end) 246 and 248, to close the belt for a wide range of waist sizes.

Belt 240 needs to be sufficiently long enough to fit around the waist of the user, such as about 3 feet, and sufficiently wide enough to encase plate 200, such as about 6 inches wide. The strips 260 are needed, about 4 in all, to sufficiently allow belt 240 to curve correctly around the waist of the user. Velcro strips 242, 246 and 248 need to be sufficiently wide and long to keep belt 240 closed and to allow for users with different sized waists, such as about 2 inches wide by 5.5 inches long for Velcro 242, and 2 inches wide by at least 5 inches long for Velcro 246 and 248, placing Velcro 242, 246 and 248 at the corners of belt 240 to allow the best possible closing capability.

The construction details of the invention as in FIGS. 12-13 are that plate 200 and acupressure points 214-222 may be made of urethane plastic from a mold or any other sufficiently rigid and strong material such as high-strength plastic, rubber and the like. The construction details of belt 240 are that the belt be made of elastic, strips 260 may be made of plastic or any other semi rigid and strong materials so as to keep the belt from folding onto itself. The Velcro strips 242, 246 and 248 may be made of Velcro, or another hook and loop system to close the belt sufficiently around the users waist.

The lower back acupressure device shown and described with reference to FIGS. 1-13 is based on how traditionally acupuncture or acupressure has been administered in China, which is to receive treatment every day (and in many cases more than once daily) for at least one month for many lower back health concerns to resolve optimally. However, due to the high expense, relative lack of cultural acceptance of acupuncture and/or acupressure in the United States, and lack of available time for most westerners to get treatment daily, in the United States treatment tends to be only administered once or twice a week, and subsequently the results are less effective then everyday treatment.

Aside from the unique design of the curved plate and affixed acupressure points, the specific health benefits of this plate and belt invention comes from receiving affordable and accessible daily acupressure treatment for lumbar 2/3 (L2/L3), lumbar 4/5 (L4/L5) and lumbar 5/sacral 1 (L5/S1) vertebral related pain, as well as sacrum and iliac related pain, without the extra expense and hassle of going for daily visits to their Oriental medicine healthcare professional. When possible, users are recommended to continue seeing their Oriental medicine healthcare professional as requested by such practitioners; however this present invention may serve as an invaluable adjunct to the care given by an Oriental medicine healthcare professional. It may also be tried as an alternative when a user suffering from lower back and/or sacral-iliac pain is unable to see an Oriental medicine healthcare professional, for one reason or another.

Although the present disclosure has been described with reference to preferred embodiments, workers skilled in the art will recognize that changes can be made in form and detail without departing from the spirit and scope of the present disclosure.

What is claimed is:

1. A lower back acupressure device for promoting healing, the device comprising:

an outer circumferential frame encompassing a void and having a vertical center plane;

a left wing permanently affixed to the circumferential frame at first and second connection points and a right wing permanently affixed to the circumferential frame at third and fourth connection points, the left and right wings located within the void and each capable of independent movement of each other and of the frame;

three horizontal pairs of acupressure protrusions, each pair of acupressure protrusions consisting of a left acupressure protrusion affixed to the left wing and a corresponding right acupressure protrusion affixed to the right wing, the left and right acupressure protrusions positioned horizontally equal distant from the vertical center plane;

a fourth horizontal pair of acupressure protrusions consisting of a left acupressure protrusion affixed to the frame left of the vertical center plane and a right acupressure protrusion affixed to the frame right of the vertical center plane, the left and right acupressure protrusion of the fourth horizontal pair of acupressure protrusions located horizontally equal distant from the vertical center plane as the first three pairs of horizontal pairs of acupressure protrusions, and a fifth horizontal pair of acupressure protrusions consisting of a left acupressure protrusion affixed to the left wing and a right acupressure protrusion affixed to the right wing, the fifth horizontal pair of acupressure protrusions positioned vertically between the fourth horizontal pair and a lowest pair of the initial three horizontal pairs of acupressure protrusions and centered about the vertical center plane at a horizontal distance greater than a horizontal distance of the first four pairs of acupressure protrusions.

2. The lower back acupressure device of claim 1, and further comprising:

a belt detachably affixed to the frame for securing the plate to a person at a proper location and a proper pressure, including securing the frame to a person such that the vertical center of the frame is aligned with a spine of the person.

3. The lower back acupressure device of claim 2, wherein the belt secures the frame to the person such that the two lowest horizontal pairs of acupressure protrusions are positioned adjacent to a sacrum and an iliac bone of the user.

4. The lower back acupressure device of claim 3, wherein the belt secures the frame to the person such that a first pair of the remaining three horizontal pairs of acupressure protrusions are positioned adjacent to a junction of lumbar vertebra 5/sacral 1 (L5/S1), a second pair at a junction of lumbar vertebra 4/lumbar vertebra 5 (L4/L5), and a third pair at a junction of lumbar vertebra 2/lumbar vertebra 3 (L2/L3).

5. The lower back acupressure device of claim 2, and further comprising:

a turbo adaptor that when connected to the belt provides additional isolated pressure to the lower back.

6. The lower back acupressure device of claim 1, wherein each of the 10 acupressure protrusions has a height greater than 0.50 inches.

7. The lower back acupressure device of claim 1, wherein each of the 10 acupressure protrusions are tapered from a base of the protrusion to a tip of the protrusion.

8. The lower back acupressure device of claim 1, and further including:

a temperature pack attached to the frame, the temperature pack including a first and a second hot/cold pack positioned within the void between the frame and the left and right wings, respectively.

9. The lower back acupressure device of claim 1, wherein the frame is contoured such that an angle of curvature between a top portion of the device and a bottom portion of the device is in the range of 120 degrees and 160 degrees.

10. A lower back acupressure device comprising:

a circumferential frame encompassing an open space and having a vertical center plane;

first and second support vessels attached to the circumferential frame and positioned within the open space, the first support vessel attached to the circumferential frame at two attachment points and the second support vessel attached to the circumferential frame at two different attachment points such that the first and second support vessels are capable of independent movement of each other and capable of independent movement of the circumferential frame:

four pairs of acupressure protrusions centered about the vertical center plane, at least the upper most three pairs of acupressure protrusions having a first acupressure protrusion positioned on the first support vessel and a second acupressure protrusion positioned on the second support vessel;

a fifth pair of acupressure protrusions having a first acupressure protrusion positioned on the first support vessel and a second acupressure protrusion positioned on the second support vessel and located vertically between a lowest and a second lowest pair of the four pairs of acupressure protrusions and centered about the vertical center plane, the fifth pair of acupressure protrusions having a horizontal distance there between greater than a horizontal distance of the four pairs of acupressure protrusions.

11. The lower back acupressure device of claim 10, and further comprising:

a belt detachably affixed to the frame for securing the frame to a person at a proper location and a proper pressure, including securing the frame to a user such that the vertical center of the frame is aligned with a spine of the user.

12. The lower back acupressure device of claim 11, wherein the belt secures the frame to a user such that the two lowest pairs of acupressure protrusions are positioned adjacent to a sacrum and an iliac bone of the user.

13. The lower back acupressure device of claim 12, wherein the belt secures the frame to the person such that a first pair of the remaining three highest pairs of acupressure protrusions are positioned adjacent to a junction of lumbar vertebra 5/sacral 1 (L5/S1), a second pair at a junction of lumbar vertebra 4/lumbar vertebra 5 (L4/L5), and a third pair at a junction of lumbar vertebra 2/lumbar vertebra 3 (L2/L3).

14. The lower back acupressure device of claim 11, and further comprising:

a turbo adaptor connected to the belt for providing additional isolated pressure to the lower back.

15. The lower back acupressure device of claim 10, wherein each of the 10 acupressure protrusions has a height greater than 0.50 inches.

16. The lower back acupressure device of claim 10, and further including:

a temperature pack attached to the frame, the temperature pack including a first and a second hot/cold pack positioned within the open space between the frame and the left and right wings, respectively.

* * * * *